United States Patent [19]

Hamilton et al.

[11] Patent Number: 4,789,679

[45] Date of Patent: Dec. 6, 1988

[54] METHOD FOR TREATING INCONTINENCE

[75] Inventors: Thomas C. Hamilton; Robin E. Buckingham, both of Harlow, England

[73] Assignee: Beecham Group p.l.c., England

[21] Appl. No.: 74,943

[22] Filed: Jul. 17, 1987

[30] Foreign Application Priority Data

Jul. 18, 1986 [GB] United Kingdom ................. 8617623

[51] Int. Cl.$^4$ ............................................. A61K 31/44
[52] U.S. Cl. ............................................. 514/353
[58] Field of Search ........................................ 514/353

[56] References Cited

U.S. PATENT DOCUMENTS

| | | | |
|---|---|---|---|
| Re. 31,244 | 5/1983 | Peterson | 514/349 |
| 4,617,311 | 10/1986 | Ho | 514/353 |
| 4,720,387 | 1/1988 | Sakamoto et al. | 514/353 X |

*Primary Examiner*—Leonard Schenkman
*Attorney, Agent, or Firm*—Jacobs & Jacobs

[57] ABSTRACT

A method for the treatment and/or prophylaxis of incontinence in mammals, which method comprises administering to the mammal an effective amount of the compound pinacidil or a pharmaceutically acceptable salt or solvate thereof.

1 Claim, No Drawings

METHOD FOR TREATING INCONTINENCE

The present invention relates to a method for the treatment and/or prophylaxis of disorders associated with smooth muscle contraction of the urinary tract.

United Kingdom Pat. No. 1489879 discloses the compound N''-Cyano- N-4-pyridyl-N'-1,2,2-trimethylpropylguanidine and, in Example 47, a process by which it can be prepared. The compound, which is referred to herein by its common name, pinacidil, is described in the patent as a hypotensive compound. In "Drugs of the Future" Vol. VI(3), 149, 1981, pinacidil is described as a vasodilator and U.S. Pat. No. 4,617,311 discloses pinacidil as a bronchodilator for use in the treatment of asthma.

It has now been discovered that pinacidil is of potential use in the treatment of disorders associated with smooth muscle contraction of the urinary tract. Such disorders include incontinence.

Accordingly, the present invention provides a method for the treatment and/or prophylaxis of disorders of the urinary tract in mammals, such as humans, which method comprises administering to the mammal in need of such treatment and/or prophylaxis an effective and/or prophylactic amount of pinacidil; or a pharmaceutically acceptable salt or solvate thereof.

Examples of a pharmaceutically acceptable salt of pinacidil include acid addition salts, for example the hydrochloride and hydrobromide salts.

Examples of a pharmaceutically acceptable solvate of pinacidil include the hydrate.

Preferably, pinacidil is in substantially pure pharmaceutically acceptable form.

Pinacidil may be prepared as described in the aforementioned U.K. patent, and pharmaceutically acceptable salts may be prepared conventionally.

The administration of pinacidil or a pharmaceutically acceptable salt thereof may be by way of oral, sublingual, transdermal or parenteral administration.

An amount effective to treat the disorders hereinbefore described depends on the usual factors such as the nature and severity of the disorders being treated and the weight of the mammal. However, a unit dose will normally contain 0.1 to 50 mg for example 0.5 to 10 mg, of pinacidil or a pharmaceutically acceptable salt thereof. Unit doses will normally be administered once or more than once a day, for example 2, 3, or 4 times a day, more usually 1 to 3 times a day, such that the total daily dose is normally in the range, for a 70 kg adult, of 0.1 to 50 mg, for example 0.5 to 10 mg, that is in the range of approximately 0.001 to 1 mg/kg/day, more usually 0.005 to 0.2 mg/kg/day.

Within the above indicated dosage range, no adverse toxicological effects are indicated.

It is greatly preferred that pinacidil or a pharmaceutically acceptable salt thereof is administered in the form of a unit-dose composition, such as a unit dose oral or parenteral composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

The present invention also provides pinacidil or a pharmaceutically acceptable salt or solvate thereof for the manufacture of a medicament for use in the treatment and/or prophylaxis of disorders of the urinary tract. Such treatment and/or prophylaxis may be carried out as hereinbefore described.

The present invention further provides a pharmaceutical composition for use in the treatment and/or prophylaxis of disorders of the urinary tract which comprises pinacidil or a pharmaceutically acceptable salt or solvate thereof and a pharmaceutically acceptable carrier.

Such compositions may be prepared in the manner as hereinbefore described.

The following pharmacological data illustrate the activity of pinacidil in a test which is indicative of compounds of potential use in the treatment of disorders of the urinary tract.

PHARMACOLOGICAL DATA

Rat Detrusor Strip Screen

Method

Male Wistar Charles River rats (Crl: WI BR) weighing 300–350 g were used.

The urinary bladder was removed and a longitudinal strip 3 mm wide was cut from the urethra to the apex of the bladder.

The strip was immediately immersed in a 20 ml bath containing Tyrode with double millimolar concentration of glucose (11.1) and with addition of sucrose (13.3 millimolar), kept at 37° C. and aerated with a mixture of $O_2$, 95% and $CO_2$, 5%.

Tyrode composition was (mM): NaCl 136.8, KCl 2.68, $CaCl_2$ 1.80, $MgSO_4 \cdot 7H_2O$ 1.05, $NaH_2PO_4 \cdot H_2O$ 0.41, $NaHCO_3$ 11.9, glucose 11.1 sucrose 13.3. The strip was in direct contact with one of the two platinum electrodes placed on the top and bottom of the organ bath. Placed under an initial tension of 2 g, the strip was then allowed to relax until a baseline of about 1 g. After a 5 min equilibration period isometric contractions were induced by a GRASS S88 2 channel stimulator using the following parameters: trains of pulses of 2 sec duration each every 100 sec; square wave pulse of volts (60–70); duration 0.7 ms and 30 Hz.

When the contractions became constant (60–90 min), the strips were exposed to the test compound, pinacidil. The isometric contractions were measured with a Basile DY1 force transducer connected to a Battaglia Rangoni 4 channel recorder. The results are expressed as per cent of contraction inhibition.

At a molar concentration of $3 \times 10^{-6}$ the mean % inhibition was 95.

We claim:

1. A method of treatment and/or prophylaxis of incontinence in mammals which comprises administering to the mammal in need of such treatment an effective amount of the compound pinacidil or a pharmaceutically acceptable salt or solvate thereof.

* * * * *